(12) United States Patent
Calenzo, Sr. et al.

(10) Patent No.: US 6,240,323 B1
(45) Date of Patent: May 29, 2001

(54) PERFORATED SIZE ADJUSTABLE BIOMEDICAL ELECTRODE

(75) Inventors: James C. Calenzo, Sr., Deerfield, NY (US); Arthur R. Eddy, Jr., Hampton, NH (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 09/132,416

(22) Filed: Aug. 11, 1998

(51) Int. Cl.$^7$ ............................................. A61N 1/04
(52) U.S. Cl. ....................... 607/142; 607/152; 600/372
(58) Field of Search ................................. 607/142, 129, 607/152; 600/372, 374, 382, 391, 392

(56) References Cited

U.S. PATENT DOCUMENTS

| | | | |
|---|---|---|---|
| 4,233,987 | * 11/1980 | Feingold | 128/639 |
| 4,331,153 | 5/1982 | Healy | 128/641 |
| 4,554,924 | 11/1985 | Engle . | |
| 4,580,339 | 4/1986 | Ioffe . | |
| 4,640,289 | * 2/1987 | Craighead | 128/639 |
| 4,674,512 | 6/1987 | Rolf | 128/640 |
| 4,757,817 | 7/1988 | Healy | 128/641 |
| 4,834,103 | 5/1989 | Heath | 128/798 |
| 5,330,527 | 7/1994 | Montecalvo et al. | 607/152 |
| 5,348,007 | 9/1994 | Hitti | 128/640 |
| 5,689,877 | 11/1997 | Grill, Jr. et al. | 29/825 |

* cited by examiner

Primary Examiner—Carl H. Layno
(74) Attorney, Agent, or Firm—Heslin & Rothenberg, P.C.

(57) ABSTRACT

A perforated biomedical electrode having a detachable portion which allows a clinician to remove a portion of the electrode to thereby reduce the effective contact size of the electrode, e.g., the effective surface area for adhering the electrode to the patient's skin and/or the effective surface area for establishing electrical contact or ground with the patient's skin depending on the particular application, e.g., for use on an adult or a child. The biomedical electrode includes a pad comprising a first portion and a predefined line of separation along which a second portion of the pad is detachable from the pad so that the pad initially comprises a first surface area for contacting a patient's skin and upon detaching the second portion from the pad, the pad comprises a second surface area for contacting the patient's skin. An electrode attaches to the first portion of the pad. Desirably, a series of slits peripherally extends around the first portion and through the pad to define the predefined line of separation. A layer of adhesive may be applied on the first surface area and a protective cover sheet may be provided for protecting the layer of adhesive. The perforated biomedical electrode may also include a top non-electrically conductive foam layer, an electrically conductive metal foil layer, and a layer of electrically conductive adhesive.

33 Claims, 3 Drawing Sheets

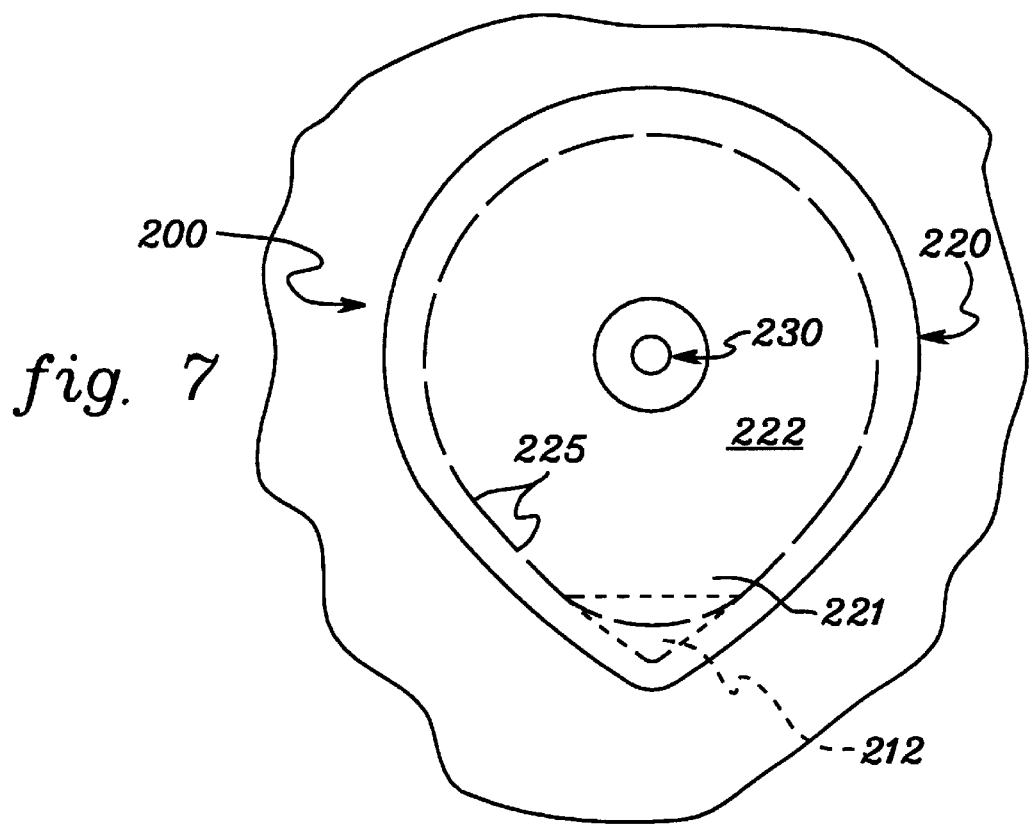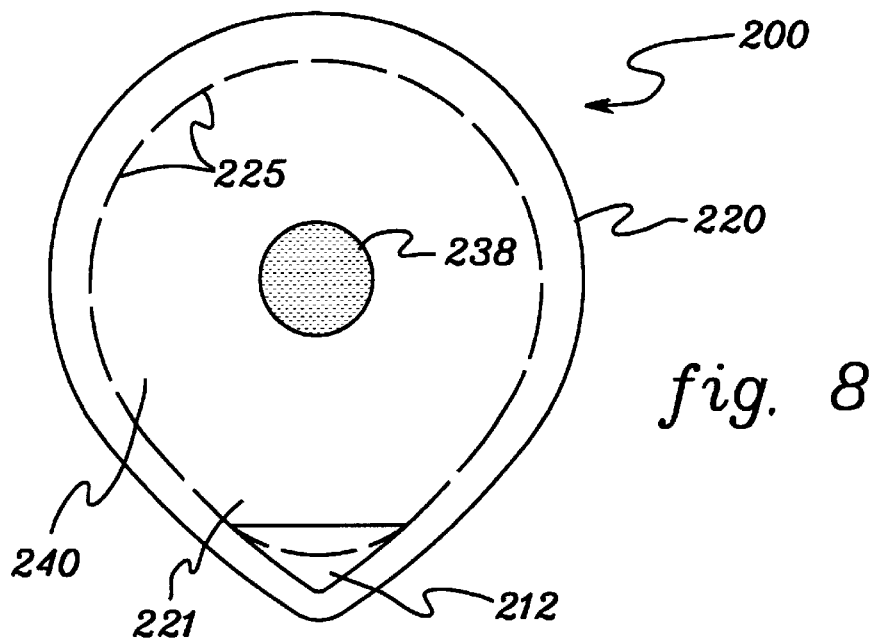

PERFORATED SIZE ADJUSTABLE BIOMEDICAL ELECTRODE

FIELD OF THE INVENTION

The present invention relates generally to biomedical electrodes. More particularly, the present invention relates to novel perforated biomedical electrodes having a surface area for contacting to a patient's skin which can be readily reduced in size depending on a particular application.

BACKGROUND INFORMATION

Biomedical electrodes are typically used in monitoring electrical impulses from the heart or brain. Conventional biomedical electrodes are generally disposable and comprise a pad member with an electrode projection on its top surface which is in electrical communication with a central portion of the bottom surface for making an electrical contact with a patient's skin. Typically, an adhesive material on the bottom surface surrounds the central portion and attaches the electrode in place. Biomedical electrodes are also typically used in providing electrical impulses for nerve or neuromuscular stimulation. Biomedical electrodes may also be used to deliver current, e.g., a defibrillation pad, in the event that the heart goes into fibrillation or to act as a ground during electrosurgery, e.g., a dispersive pad. Examples of such prior art biomedical electrodes are disclosed in U.S. Pat. Nos. 4,674,512 to Rolf; 4,834,103 to Heath; and 5,330,527 to Montecalvo et al.

Examples of biomedical electrodes which are configured to more securely attach an electrical lead wire to the electrode include, U.S. Pat. Nos. 4,331,153 and 4,757,817, both to Healy. In particular, the patents to Healy disclose an EKG electrode pad having a cut which allows an auxiliary portion of the pad to be lifted up and placed over the electrical lead wire which attaches to an electrode projection of the electrode.

U.S. Pat. No. 5,348,007 to Hitti discloses a biomedical electrode that will not easily be pulled from the skin of a patient when a force is exerted between the electrical lead wire and the patient. In particular, the biomedical electrode disclosed in Hitti includes a contact portion connected to a conductive bridge portion. The bridge portion is provided with a series of perforations or slits separated by small connections. The perforations form a break away means for the bridge portion which is used to pull the bridge portion apart, allowing it to expand, either immediately before or after the contact portion is applied to the patient's skin.

A drawback with the above-noted biomedical electrodes is that they are configured with a single or fixed surface area for contacting to a patient's skin. For example, when used in monitoring electrical impulses from a patient's heart or brain, a large number of electrodes are required to be attached to the patient's skin. Biomedical electrodes which have a fixed surface area for contacting to a patient's skin limit how close the biomedical electrodes can be spaced from each other. Such biomedical electrodes are also configured having a single or fixed surface area for establishing an electrical contact or ground with the patient's skin.

In addition, biomedical electrodes having the same contact size are typically packaged and sold in large volumes, e.g., to hospitals or government agencies. This limits purchases of biomedical electrodes having different contact sizes, and particularly, to less frequently used biomedical electrode sizes.

Therefore, there is a need for perforated biomedical electrodes having a surface area for contacting to a patient's skin which can be readily reduced in size allowing the electrode to be better suited for a particular application, e.g., initially being sized for use on an adult patient while having a readily removable portion that can be detached so that the biomedical electrode can be reduced in size for use on a child or small adult.

SUMMARY OF THE INVENTION

Pursuant to the present invention, the shortcomings of the prior art are overcome and additional advantages provided through the provision of a biomedical electrode having one or more detachable portions which a clinician can readily remove to thereby reduce the contact size of the electrode, e.g., to reduce the effective area for adhering the electrode to the patient's skin and/or to reduce the effective area for establishing electrical contact or ground with the patient's skin.

One embodiment of a biomedical electrode according to the present invention includes a pad comprising a first portion, a second portion, and a predefined means for detaching the second portion from the pad so that the pad with the second portion comprises a first surface area for contacting a patient's skin and upon detaching the second portion from the pad, the pad comprises a second surface area for contacting the patient's skin. An electrode is operably attached to the first portion of the pad.

The predefined means for detaching may comprise a predefined line of separation and the second portion is detachable from the pad along the predefined line of separation. The predefined means for detaching may also peripherally extend around the first portion. For example, the pad may be disk-shaped, the first portion may be disk-shaped, and the second portion may be annular-shaped.

The predefined means for detaching may further comprise a series of apertures which extends through the pad. Desirably, the biomedical electrode includes a layer of pressure-sensitive adhesive disposed on a portion of the first surface area and a protective cover sheet releasably attachable to the layer of adhesive.

In another embodiment of the biomedical electrode, an electrically conductive layer is disposed between the first surface area and the adhesive layer, and the predefined means for detaching comprises a series of apertures which extends through the pad and the electrically conductive layer.

In still another embodiment of the invention, the first portion comprises a top surface and a bottom surface, and the electrode comprises an upper electrical projection extending from the top surface and a lower planar member disposed below the bottom surface. A porous member may be disposed on a bottom surface of the lower planar member and an electrically conductive jelly may be absorbed into the porous member.

A further embodiment of the present invention comprises a method of producing a biomedical electrode comprising the steps of providing a pad having a first portion, defining means for detaching a second portion from the pad so that the pad with the second portion has a first surface area for contacting a patient's skin and upon detaching the second portion from the pad, the pad has a second surface area for contacting the patient's skin, providing an electrode, and attaching the electrode to the first portion.

BRIEF DESCRIPTION OF THE DRAWINGS

These and other objects, advantages and features of the present invention will be more readily understood from the following detailed description of certain preferred embodiments of the present invention, when considered in conjunction with the accompanying drawings in which:

FIG. 7 is a top view of an alternative embodiment of a perforated biomedical electrode according to the present invention; and FIG. 8 is a bottom view of the perforated biomedical electrode shown in FIG. 7.

DETAILED DESCRIPTION OF THE PREFERRED EMBODIMENTS

Figure 1:
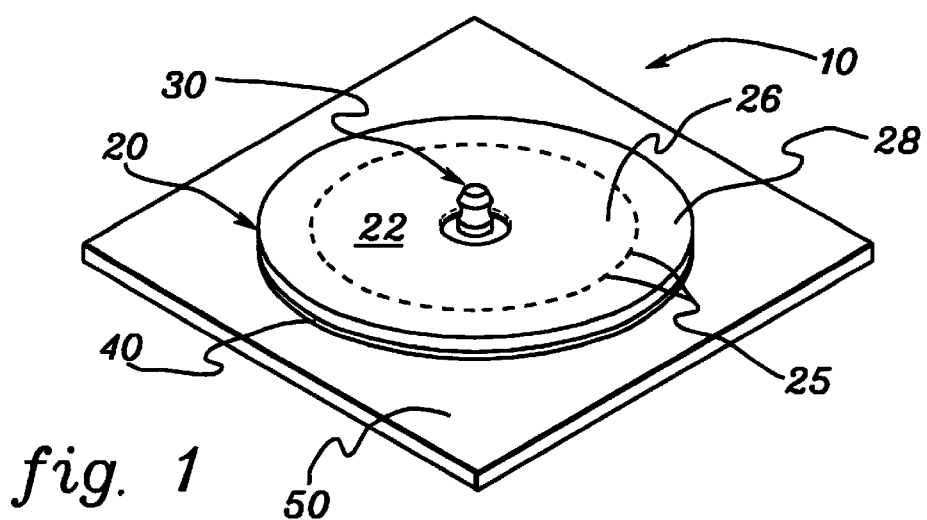
FIG. 1 is a perspective view of one embodiment of a perforated biomedical electrode according to the present invention.
Figure 2:
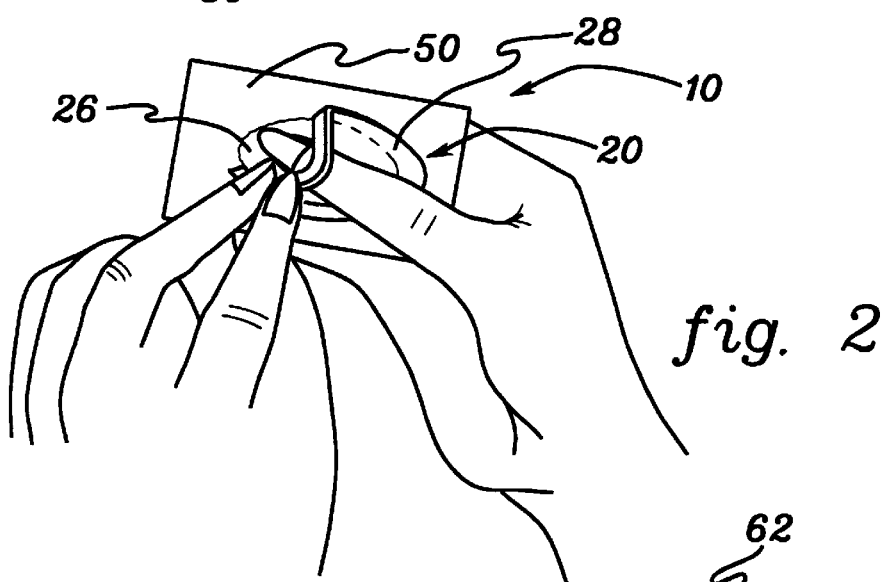
FIG. 2 is a perspective view of the perforated biomedical electrode shown in FIG. 1 in which a detachable portion of the electrode is illustrated being removed.

With reference to FIGS. 1 and 2, therein illustrated is one embodiment of a perforated biomedical electrode 10 constructed in accordance with the principles of the present invention. The novel construction of perforated biomedical electrode 10 allows a clinician to readily reduce the contact surface size of perforated biomedical electrode 10 prior to use as shown in FIG. 2.

For example, perforated biomedical electrode 10 may be used with monitoring devices including cardioscopes, electrocardiographs, and electrocardiograms for monitoring the operation of the heart, with stimulating devices including Transcutaneous Electrical Nerve Stimulation (TENS) or Neuromuscular Stimulation (NMS), as well as with therapeutic devices. The perforated biomedical electrode may also be used with defibrillation devices, as well as with electrosurgical instruments.

Figure 3:
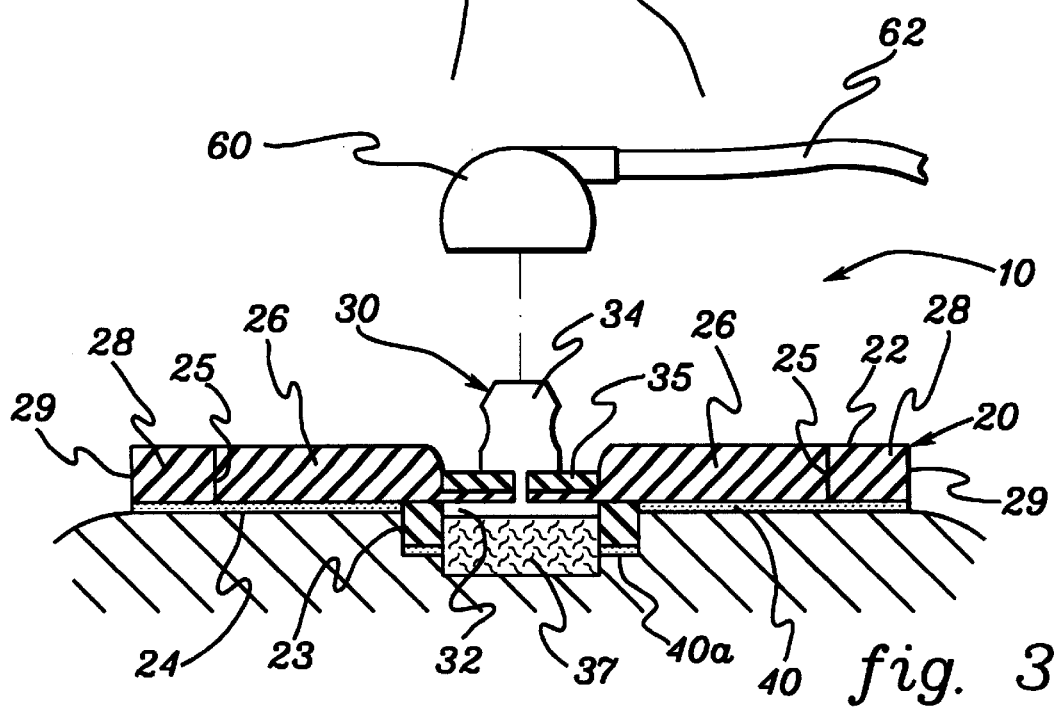
FIG. 3 is a cross-sectional view of the perforated biomedical electrode, shown in FIG. 1, attached to the skin of a patient.

With reference to FIGS. 1 and 3, illustrated perforated biomedical electrode 10 includes a disk-shaped pad 20 having a top surface 22, a bottom surface 24 (FIG. 3), and a surrounding edge 29 (FIG. 3). Pad 20 further includes an inner, disk-shaped portion 26 and an outer, annular, detachable portion 28. An electrode 30 is attached to inner portion 26, and a pressure-sensitive adhesive layer 40 is disposed on bottom surface 24 (FIG. 3) of pad 20.

Pad 20 may include a series of apertures 25 which extends from top surface 22 to bottom surface 24 (FIG. 3) and along which outer detachable portion 28 is separable from pad 20. The series of apertures 25 form a predefined detachable means or predefined line of separation between outer detachable portion 28 and inner portion 26 so that first and second portions are sufficiently attached together to act as one, and so that outer detachable portion 28 may be readily and cleanly removed from inner portion 26 along the predefined line of separation by a clinician. Desirably, the series of apertures 25 include a series of elongated slits.

While apertures 25 are illustrated as slits in FIGS. 1–3, from the present description it will be appreciated by those skilled in the art that apertures 25 can include a series of circular holes, elongated openings, or other suitable shaped passageways which allow detachment of a portion of the biomedical electrode. Furthermore, the apertures need not extend completely through the pad so long as a portion of the biomedical electrode may be readily detached along the predefined line of separation or break line. For example, the pad may have a reduced thickness which defines the line of separation along which the detachable portion is separable from the pad. It will also be appreciated by those skilled in the art that pad 20 may be of any suitable shape, e.g., oval, square, or rectangle. In addition, it will be appreciated by those skilled in the art that the predefined detachable means need not peripherally extend completely around the first or inner portion of the biomedical electrode. For example, a perforated biomedical electrode may be provided with a predefined detachable means which extends from one edge portion of the pad to an opposite edge portion of the pad, e.g., a rectangular-shaped pad having one or more readily detachable end portions.

Pad 20 may be formed from an electrically insulating or non-conductive material which is flexible to conform to a skin surface and/or flex with movement of the patient's skin. For example, pad 20 can be formed from a sheet of plastic foam, such as foamed polyurethane, polyethylene, or foam rubber, etc. Perforated biomedical electrode 10 may further include a release or protective cover sheet 50 (FIGS. 1 and 2) disposed on adhesive layer 40 for protecting adhesive layer 40. Protective cover sheet 50 may be removed or peeled off to expose pressure-sensitive adhesive layer 40 just prior to use. The protective cover sheet can comprise a suitable thin, transparent or opaque, plastic material. In addition, pad 20 may include a pull tab which can be easily grasped by a clinician for removing the protective cover sheet.

With reference to FIGS. 1 and 3, in one mode of use, release sheet 50 is removed from perforated biomedical electrode 10 and the biomedical electrode is attached to the skin of a patient by means of pressure-sensitive adhesive layer 40 (FIG. 1), e.g., for use on a patient (FIG. 3).

Figure 4:
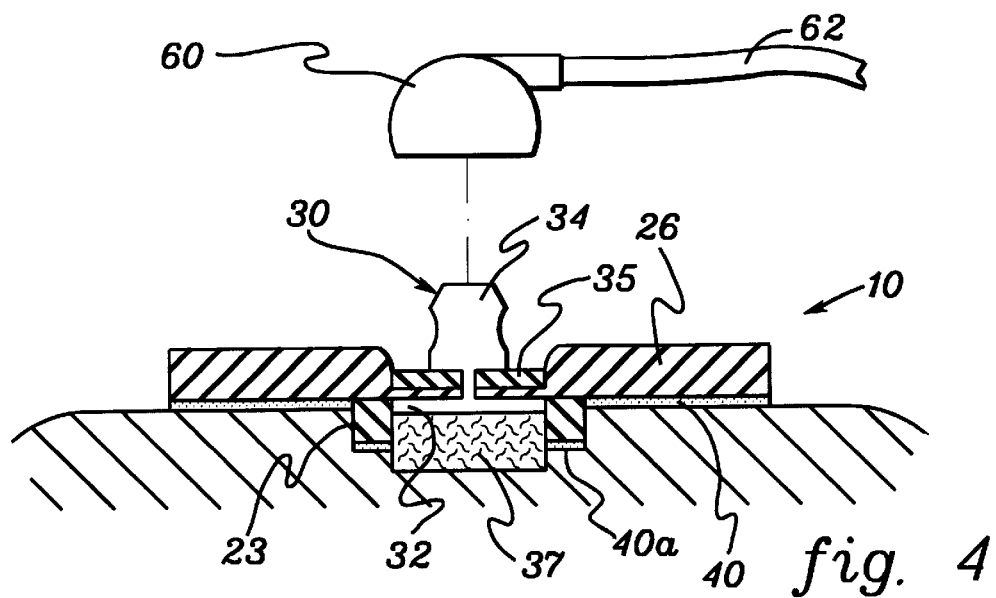
FIG. 4 is a cross-sectional view of the perforated biomedical electrode shown in FIG. 2 in which the detachable portion has been removed and the reduced size biomedical electrode is attached to the skin of a child.

With reference to FIGS. 2 and 4, in another mode of use, a clinician can easily remove outer detachable portion 28 of perforated biomedical electrode 10 prior to removal of protective cover sheet 50, as shown in FIG. 2. Subsequently, protective cover sheet 50 can be removed from the inner portion, and the reduced size biomedical electrode can be attached to the skin of a patient by means of pressure-sensitive adhesive layer 40, e.g., for use on a child or a small adult (FIG. 4).

As shown in FIG. 3, in one preferred embodiment of perforated biomedical electrode 10, outer detachable portion 28 comprises outer circular edge 29, and the series of apertures 25 are concentrically disposed so that the outer detachable portion 28 has a width, e.g., about one-third the distance from outer circular edge 29 to the center of inner portion 26.

With reference to FIGS. 3 and 4, electrode 30 may comprise a generally inverted T-shaped cross-section having a bottom planar member 32 and an upwardly extending electrical projection 34 which extends through a hole in pad 20. Electrode 30 may comprise a metal, an electrically conductive plastic, or other suitable electrically conductive materials or combinations thereof. In certain electrode designs, it may be useful to have a collar 35 which operably attaches to electrical projection 34 to retain electrode 30 to pad 20. Perforated biomedical electrode 10 can be connected to a monitoring or stimulating device via an electrical connector 60 of an electrical lead wire 62. Desirably, electrical connector 60 is readily and releasably attachable to electrical projection 32 in a snap-fit manner. Alternatively, it will be appreciated by those skilled in the art that other means for connecting the perforated biomedical electrode to a monitoring or stimulating device may be readily employed. For example, the electrode may have an electrically conductive tab-type connector means which attaches to an alligator clip type termination on the leadwire. Other types of connector means, depending upon the biomedical electrode configuration, may also employ the perforated biomedical electrode design.

Advantageously, a porous member 37 may be disposed on the bottom surface of planar member 32 for receiving and absorbing an electrically conductive fluid or jelly, e.g., saline gel, or other equally suitable medium, to provide a conductive path between the electrode and the skin of the patient. Perforated biomedical electrode 10 may also comprise an annular ring 23 disposed around porous member 37 to contain the conductive medium. Ring 23 may be fabricated from any suitable material, and is desirably formed of the same material as pad 20 and secured to pad 20 with a layer of adhesive therebetween. Desirably, the bottom portion of ring 23 includes an adhesive layer 40a. While an electrically conductive fluid or jelly can be applied to the electrode prior to use, the perforated biomedical electrodes of the present invention can be manufactured and sold with an electrically conductive fluid or jelly absorbed into the porous pad and protected by the protective cover sheet to prevent the electrically conductive fluid or jelly from drying out.

Figure 5:
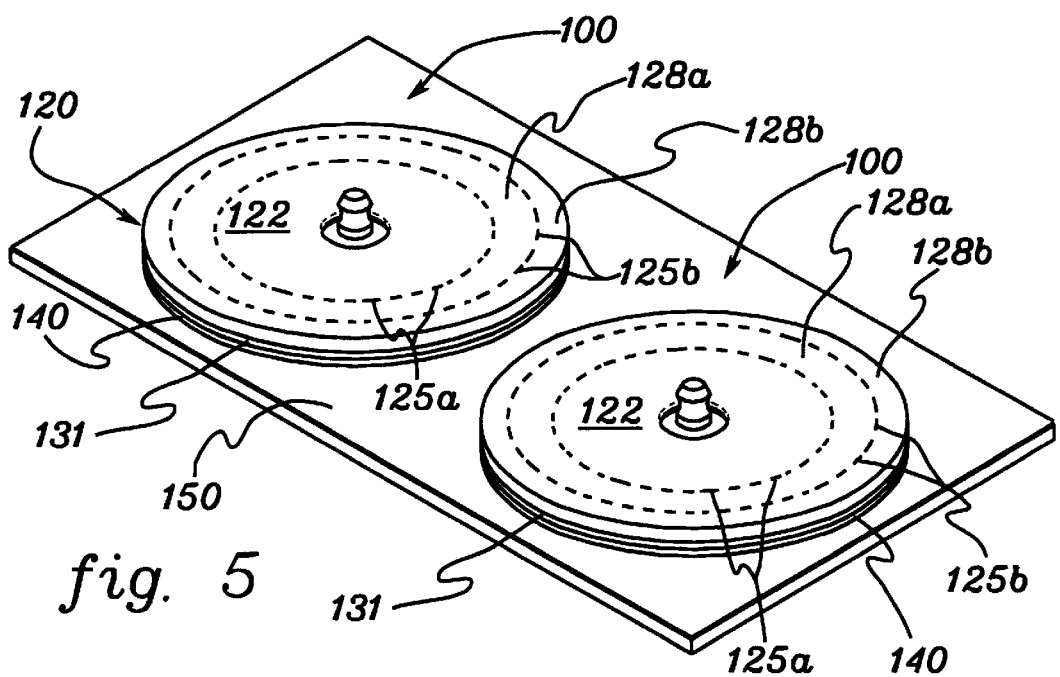
FIG. 5 is a perspective view of an alternative embodiment of a perforated biomedical electrode according to the present invention in which a plurality of perforated biomedical electrodes is attached to a single release or protective cover sheet.

FIG. 5 illustrates an alternative embodiment of the present invention for a perforated biomedical electrode 100 having a plurality of outer detachable portions 128a and 128b. As shown in FIG. 5, a plurality of perforated biomedical electrodes 100 can be disposed on a single release or protective cover sheet 150.

Figure 6:
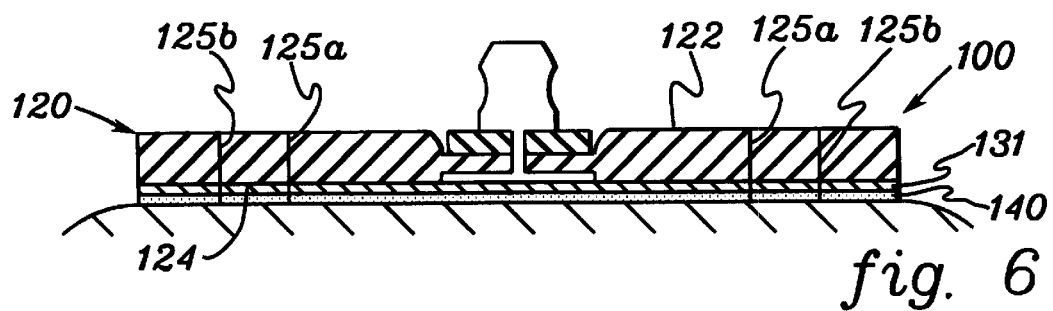
FIG. 6 is a cross-sectional view of the perforated biomedical electrode, shown in FIG. 5, attached to the skin of a patient.

As best shown in FIGS. 5 and 6, illustrated perforated biomedical electrode 100 is desirably suitable for nerve and/or neuromuscular stimulation and includes a bottom surface which provides a ground to transfer electrical impulses to a patient's skin. The bottom surface can be readily reduced in size to one of three different sizes depending on the particular application.

In this illustrated embodiment, perforated biomedical electrode 100 includes a disk-shaped pad 120 having a top surface 122 and a bottom surface 124. An electrically conductive layer 131 is attached to bottom surface 124 of pad 120, and an electrically conductive pressure-sensitive adhesive layer 140 is disposed on the bottom surface of electrically conductive layer 131.

Pad 120 and electrically conductive layer 131 further comprise a first series of apertures 125a, and a second series of apertures 125b, which extend from top surface 122 of pad 120 to a bottom surface of electrically conductive layer 131. Desirably, first series of apertures 125a and second series of apertures 125b are concentrically aligned.

The electrically conductive layer may be a flexible metal foil and the electrically conductive pressure-sensitive adhesive layer may include an electrically conductive gel. By removing one or more of outer portions 128a and 128b, biomedical electrode 100 is provided with three different effective biomedical electrode sizes. In this illustrated embodiment, the area of contact between the biomedical electrode and the patient's skin can be incrementally reduced by removing one or both outer portions, thereby varying the resistance or impedance between the biomedical electrode and the patient's skin.

Other embodiments of the perforated biomedical electrode design according to the present invention may offer additional enhancements. For example, FIG. 7 illustrates a perforated teardrop-shaped biomedical electrode 200 placed on a patient's skin surface. Biomedical electrode 200 includes a pad 220 having a main portion 222 and a pull tab portion 221. A series of aperatures 225 extends through portions 221 and 222 of pad 220. An electrode 230 may be centered on main portion 222.

As shown in FIG. 8, an adhesive 240 may be cast over the bottom surface of biomedical electrode 200 and a conductive jelly 238 may be centered and aligned with electrode 230.

The bottom surface of tab portion 221 of pad 220 contains a generally triangular-shaped release sheet portion 212 which prevents adhesive 240 on a portion of tab portion 221 from adhering to the patient's skin. Generally, triangular-shaped release sheet portion 212 may be made by using a back slit die cutting operation during the manufacturing process of biomedical electrode 200 attached to a release sheet. Series of aperatures 225 may also extend through a portion of triangular-shaped release sheet portion 212. Desirably, pull tab portion 221 allows a clinician to slid a finger or thumb underneath pull tab portion 221, grasp the tab with the thumb and finger and peel the biomedical electrode off of the patient's skin.

From the present description, it will be appreciated by those skilled in the art that while the embodiments of the present invention are described and illustrated as being non-invasive or externally applied to the patient's skin, the concept of perforated biomedical electrodes can be equally suitable to invasive or internally applied biomedical electrodes.

Thus, while several embodiments of the present invention have been illustrated and described, it will be appreciated by those skilled in the art that many changes and modifications may be made thereunto without departing from the spirit and scope of the invention.

What is claimed is:

1. A biomedical electrode comprising:

a pad comprising a first portion, a second portion, and a predefined means for detaching said second portion from said pad, so that said pad with said second portion comprises a first surface area for contacting a patient's skin and upon detaching said second portion from said pad, said pad comprises a second surface area for contacting the patient's skin, said predefined means for detaching peripherally extending around said first portion; and an electrode attached to said first portion of said pad.

2. The biomedical electrode according to claim 1, wherein said predefined means for detaching comprises a predefined line of separation and said second portion is detachable from said pad along said predefined line of separation.

3. The biomedical electrode according to claim 1, wherein said first portion comprises a top surface and a bottom surface said electrode comprises an upper electrical projection extending from said top surface and a lower planar member disposed below said bottom surface, and further comprising a porous member disposed on a bottom surface of said lower planar member.

4. The biomedical electrode according to claim 1, wherein said pad is disk-shaped, said first portion is disk-shaped, and said second portion is annular-shaped.

5. The biomedical electrode according to claim 1, wherein said second portion comprises one or more detachable portions.

6. The biomedical electrode according to claim 1, wherein said pad comprises a plurality of concentric predefined means for detaching.

7. The biomedical electrode according to claim 1, wherein predefined means for detaching comprises said pad comprising a series of apertures which extends through said pad.

8. A biomedical electrode comprising:
a pad comprising a first portion, a second portion, and a predefined means for detaching said second portion from said pad so that said pad with said second portion comprises a first surface area for contacting a patient's skin and upon detaching said second portion from said pad, said pad comprises a second surface area for contacting the patient's skin;
a layer of pressure-sensitive electrically conductive adhesive disposed on a portion of said first surface area;
an electrode attached to said first portion of said pad; and
an electrically conductive layer disposed between said first surface area and said adhesive layer.

9. The biomedical electrode according to claim 8, further comprising a protective cover sheet releasably attachable to said layer of adhesive.

10. The biomedical electrode according to claim 8, wherein said second portion comprises one or more detachable portions.

11. The biomedical electrode according to claim 8, wherein said predefined means for detaching peripherally extends around said first portion.

12. The biomedical electrode according to claim 8, wherein said predefined means for detaching comprises a series of apertures which extends through said pad and said electrically conductive layer.

13. The biomedical electrode according to claim 12, wherein said pad comprises a non-electrically conductive foam material and said electrically conductive layer comprises a metal foil.

14. A biomedical electrode comprising:
a pad comprising a first portion, a second portion, and a predefined means for detaching said second portion from said pad so that said pad with said second portion comprises a first surface area for contacting a patient's skin and upon detaching said second portion from said pad, said pad comprises a second surface area for contacting the patient's skin, said first portion comprising a top surface and a bottom surface;
an electrode attached to said first portion of said pad said electrode comprising an upper electrical projection extending from said top surface and a lower planar member disposed below said bottom surface; and
a porous member disposed on a bottom surface of said lower planar member.

15. The biomedical electrode according to claim 14, further comprising a layer of pressure-sensitive adhesive disposed on a portion of said first surface area.

16. The biomedical electrode according to claim 15, further comprising an electrically conductive jelly absorbed into said porous member.

17. The biomedical electrode according to claim 16, further comprising a protective cover sheet which releasably attaches to said layer of adhesive and which covers said porous member.

18. The biomedical electrode of claim 14, wherein said second portion comprises one or more detachable portions.

19. A biomedical electrode comprising:
a pad comprising a first portion, a second portion, and a predefined means for detaching said second portion from said pad so that said pad with said second portion comprises a first surface area for contacting a patient's skin and upon detaching said second portion from said pad, said pad comprising a second surface area for contacting the patient's skin, said predefined means for detaching extending through a pull tab portion of said pad for assisting in removal of said biomedical electrode from the patient's skin; and
an electrode attached to said first portion of said pad.

20. The biomedical electrode of claim 19, wherein said second portion comprises one or more detachable portions.

21. A method for producing a biomedical electrode comprising:
providing a pad comprising a first portion;
defining means for detaching a second portion from said pad so that said pad with said second portion comprises a first surface area for contacting a patient's skin and upon detaching said second portion, said pad comprises a second surface area for contacting the patient's skin;
providing an electrode;
attaching said electrode to said first portion; and
wherein said means for detaching peripherally extends around said first portion.

22. The method according to claim 21, wherein said means for detaching comprises a line of separation and said second portion is detachable from said pad along said line of separation.

23. The method according to claim 21, wherein said second portion comprises one or more detachable portions.

24. A biomedical electrode comprising:
an electrode pad comprising a first portion, a second portion, and a predefined means for detaching said second portion from said electrode pad so that said electrode pad with said second portion comprises a first surface area for contacting a patient's skin and upon detaching said second portion from said electrode pad, said electrode pad comprises a second surface area for contacting the patient's skin, and
an electrode attached to said first portion of said electrode pad, said second portion having no attached electrode.

25. The biomedical electrode according to claim 24, wherein said second portion comprises one or more detachable portions.

26. The biomedical electrode of claim 24, further comprising a layer of pressure-sensitive electrically conductive adhesive disposed on a portion of said first surface area.

27. The biomedical electrode according to claim 24, wherein said first portion comprises a top surface and a bottom surface, said electrode comprises an upper electrical projection extending from said top surface and a lower planar member disposed below said bottom surface, and further comprising a porous member disposed on a bottom surface of said lower planar member.

28. A biomedical electrode consisting of:
a pad comprising a first portion, a second portion, and a predefined means for detaching said second portion from said pad so that said pad with said second portion comprises a first surface area for contacting a patient's skin and upon detaching said second portion from said pad, said pad comprises a second surface area for contacting the patient's skin; and an electrode attached to said first portion of said pad.

29. The biomedical electrode according to claim 28, wherein said second portion comprises one or more detachable portions.

30. The biomedical electrode of claim 28, further comprising a layer of pressure-sensitive electrically conductive adhesive disposed on a portion of said first surface area.

31. The biomedical electrode according to claim 28, wherein said first portion comprises a top surface and a bottom surface, said electrode comprises an upper electrical projection extending from said top surface and a lower planar member disposed below said bottom surface and further comprising a porous member disposed on a bottom surface of said lower planar member.

32. A method for producing a biomedical electrode comprising:

providing an electrode pad comprising a first portion;

defining means for detaching a second portion from said electrode pad so that said electrode pad with said second portion comprises a first surface area for contacting a patient's skin and upon detaching said second portion, said pad comprises a second surface area for contacting the patient's skin;

providing an electrode; and attaching said electrode to said first portion while not attaching an electrode to said second portion.

33. A method for producing a biomedical electrode consisting of:

providing a pad comprising a first portion;

defining means for detaching a second portion from said pad so that said pad with said second portion comprises a first surface area for contacting a patient's skin and upon detaching said second portion, said pad comprises a second surface area for contacting the patient's skin;

providing an electrode; and attaching said electrode to said first portion.

* * * * *